(12) United States Patent
Mutti et al.

(10) Patent No.: US 7,179,909 B2
(45) Date of Patent: Feb. 20, 2007

(54) PROCESS FOR THE MANUFACTURE OF A PRODUCT OF THE THIAZOLO [3,4,5-DE] [4,1]BENZOTHIAZEPINE TYPE

(75) Inventors: Stephane Mutti, Le Perreux sur Marne (FR); Joel Malpart, Olivet (FR); Michel Lavigne, Chilly Mazarin (FR); Michel Cheve, Soisy sur Seine (FR)

(73) Assignee: Aventis Pharma S.A., Paris (FR)

( * ) Notice: Subject to any disclaimer, the term of this patent is extended or adjusted under 35 U.S.C. 154(b) by 246 days.

(21) Appl. No.: 11/005,224

(22) Filed: Dec. 6, 2004

(65) Prior Publication Data

US 2005/0165002 A1  Jul. 28, 2005

Related U.S. Application Data

(60) Provisional application No. 60/543,232, filed on Feb. 10, 2004.

(30) Foreign Application Priority Data

Dec. 12, 2003  (FR) .................................. 03 14574

(51) Int. Cl.
*C07D 513/06* (2006.01)

(52) U.S. Cl. ...................................................... 540/548

(58) Field of Classification Search ................. 540/548
See application file for complete search history.

(56) References Cited

FOREIGN PATENT DOCUMENTS

WO  WO99/05147  2/1999

*Primary Examiner*—Bruck Kifle
(74) *Attorney, Agent, or Firm*—Irving Newman

(57) ABSTRACT

Novel processes for the preparation of a compound of the thiazolo[3,4,5-de] [4,1]benzothiazepine type and in particular of 2-imino-9-trifluoromethyl-4,5-dihydro-2H,7H-thiazolo[3,4,5-de] [4,1]benzothiazepine 6,6-dioxide methanesulfonate and (R,S)-2-imino-9-trifluoromethyl-4,5-dihydro-2H,7H-thiazolo[3,4,5-de] [4,1]benzothiazepine 6-oxide and its enantiomers and their pharmaceutically acceptable salts.

14 Claims, No Drawings

PROCESS FOR THE MANUFACTURE OF A PRODUCT OF THE THIAZOLO [3,4,5-DE] [4,1]BENZOTHIAZEPINE TYPE

CROSS-REFERENCE TO RELATED APPLICATIONS

This application claims the benefit of U.S. Provisional Application 60/543,232, filed Feb. 10, 2004, as well as the benefit of priority from French Patent Application No. 0314574 filed Dec. 12, 2003.

BACKGROUND OF THE INVENTION

The present invention relates to methods for preparing compounds of the thiazolo[3,4,5-de] [4,1]benzothiazepine type and in particular of 2-imino-9-trifluoromethyl-4,5-dihydro-2H,7H-thiazolo[3,4,5-de] [4,1]benzothiazepine 6,6-dioxide methanesulfonate and of (R,S)-2-imino-9-trifluoromethyl-4,5-dihydro-2H,7H-thiazolo[3,4,5-de] [4,1] benzothiazepine 6-oxide and these enantiomers and their pharmaceutically acceptable salts. These products are described in patent application WO 99/05147. These products are known and are particularly useful for the treatment and/or prevention of convulsions and diseases linked to glutamatergic transmission. They are especially useful for treating and/or preventing ischemias (such as focal or global ischemia) following cerebral vascular accidents such as thromboembolic and hemorrhagic stroke, cardiac arrest, arterial hypotension, cardiac, vascular or pulmonary surgery or severe hypoglycemia, in the treatment of the effects caused by anoxia, whether it is perinatal or subsequent to drowning, a high pressure or cerebrospinal lesions, for treating or preventing the progression of neurodegenerative diseases, HUNTINGTON's chorea, of ALZHEIMER's disease and other dementias, of amyotrophic lateral sclerosis or of other motor neurone diseases, of olivopontocerebella atrophy and of PARKINSON's disease, against epileptogenic (epilepsy) and/or convulsive manifestations, for the treatment of cerebral or spinal traumas, of traumas linked to degeneration of the inner ear or of the retina, of tinnitus, of anxiety, of depression, of schizophrenia, of TOURETTE's syndrome, of hepatic encephalopathies, of sleep disorders, of attention deficit disorders, of disorders of hormonal conditions (excess secretion of GH or LH, secretion of corticosterone), as analgesics, anti-inflammatory agents, antianorectics, antimigraine drugs, antiemetics and for treating poisoning by neurotoxins and neurological disorders associated with viral diseases such as meningitis and viral encephalitis, AIDS, rabies, measles and tetanus. These compounds are useful for the prevention of, tolerance to and dependency on the symptoms of withdrawal from drugs and alcohol, and of inhibition of addiction to and dependence on opiates, barbiturates, amphetamine and benzodiazepines. They may also be used in the treatment of deficiencies linked to mitochondrial abnormalities such as mitochondrial myopathy, LEBER's syndrome, WERNICKE's encephalopathy, RETT's syndrome, homocysteinemia, hyperprolinemia, hydroxybutyric-aminoaciduria, saturine encephalopathy (chronic lead poisoning) and sulfite oxidase deficiency.

SUMMARY OF THE INVENTION

The present invention relates to the development of a process for the synthesis of 2-imino-9-trifluoromethyl-4,5-dihydro-2H,7H-thiazolo[3,4,5-de] [4,1]benzo-thiazepine 6,6-dioxide methanesulfonate and of (R,S)-2-imino-9-trifluoromethyl-4,5-dihydro-2H,7H-thiazolo[3,4,5-de] [4,1] benzothiazepine 6-oxide and these enantiomers (S)-2-imino-9-trifluoromethyl-4,5-dihydro-2H,7H-thiazolo[3,4,5-de] [4,1]benzothiazepine 6-oxide methanesulfonate and (R)-2-imino-9-trifluoromethyl-4,5-dihydro-2H,7H-thiazolo[3,4,5-de] [4,1]benzothiazepine 6-oxide methanesulfonate compatible with large-scale production.

DETAILED DESCRIPTION

Patent application WO 99/05147 describes a general method of synthesis which is difficult to transpose to the industrial scale for production in a large quantity. The synthesis is described in examples 10, 11 and 13 of patent application WO 99/05147 and most generally in the process part of the description.

The present invention has made it possible to optimize the synthesis in terms of number of steps and of yield, thus allowing large-scale production, which could not be envisaged using the data and operating conditions developed in patent application WO 99/05147.

Indeed, the novel process of synthesis has made it possible to reduce the number of intermediates isolated and to suppress the purifications by chromatography on silica.

The method of synthesis developed in patent application WO 99/05147 consists in obtaining 2-imino-9-trifluoromethyl-4,5-dihydro-2H,7H-thiazolo[3,4,5-de] [4,1]benzothiazepine 6,6-dioxide methanesulfonate in 9 steps from 4-trifluoromethylaniline and according to the reaction scheme (I) below Scheme (I)

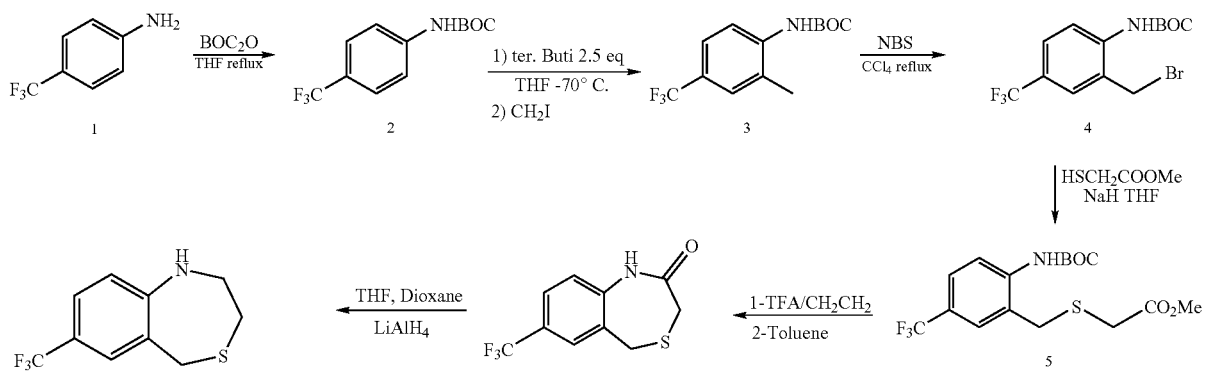

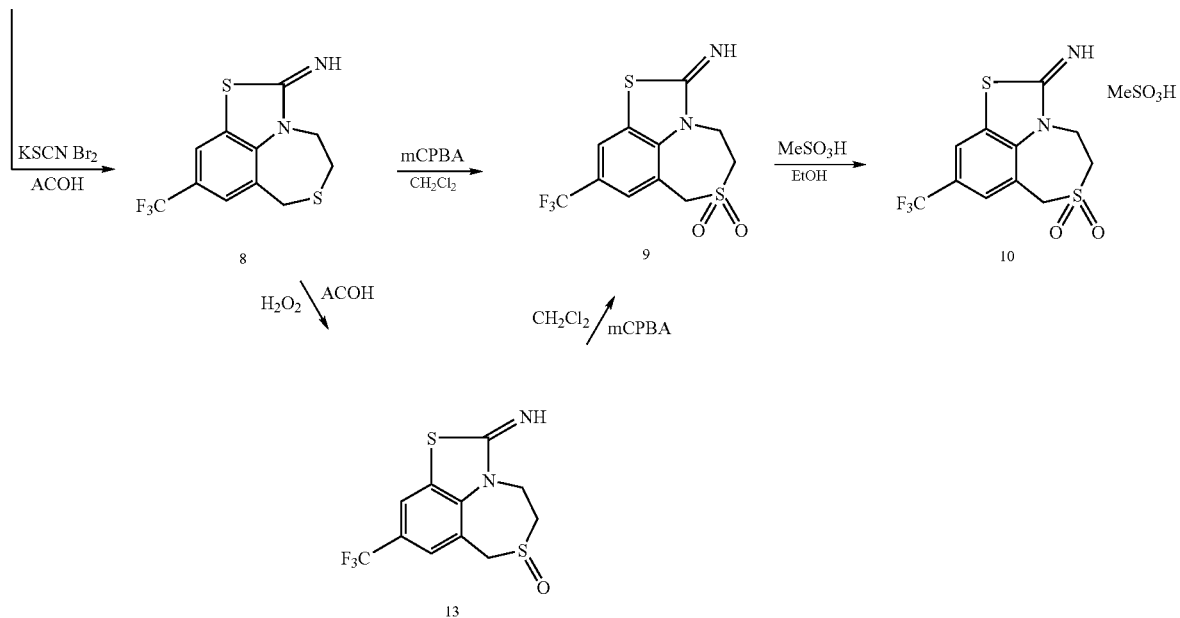

Product 1 is protected according to conventional methods with a BOC group with di-tert-butyl dicarbonate in THF under reflux in order to obtain product 2. Product 2 is converted to product 3 with tert-butyllithium which is highly unstable. The methyl functional group is brominated with N-bromosuccinimide in order to obtain product 4. The sulfur-containing chain is introduced with methyl thioglycolate in the presence of sodium hydride in order to obtain the intermediate 5. This intermediate 5 is cyclized in the presence of trifluoroacetic acid. The amide functional group of the intermediate 6: 7-trifluoromethyl-1,5-dihydro-3H-[4,1]benzothiazepin-2-one is reduced to an amine in the presence of lithium tetrahydroaluminate in order to obtain the intermediate 7: 7-trifluoromethyl-1,2,3,5-tetrahydro-[4,1]benzothiazepine. The third ring is introduced in the presence of potassium thiocyannate and bromine in acetic acid. The key intermediate 8: 2-imino-9-trifluoromethyl-4,5-dihydro-2H,7H-thiazolo[3,4,5-de] [4,1]benzothiazepine is then obtained in 7 steps.

The intermediate 8 makes it possible to obtain the final product 2-imino-9-trifluoromethyl-4,5-dihydro-2H,7H-thiazolo[3,4,5-de] [4,1]benzothiazepine 6,6-dioxide methanesulfonate but also (R,S)-2-imino-9-trifluoromethyl-4,5-dihydro-2H,7H-thiazolo[3,4,5-de] [4,1]benzothiazepine 6-oxide and its enantiomers.

The present invention has made it possible to optimize each of these steps according to the reaction scheme (II) and in particular to reduce the number of synthesis steps thereof and to use other synthesis intermediates, industrial reagents and to carry out the cyclization of the $2^{nd}$ ring directly in one step, this being by eliminating purifications by chromatography.

Scheme (II)

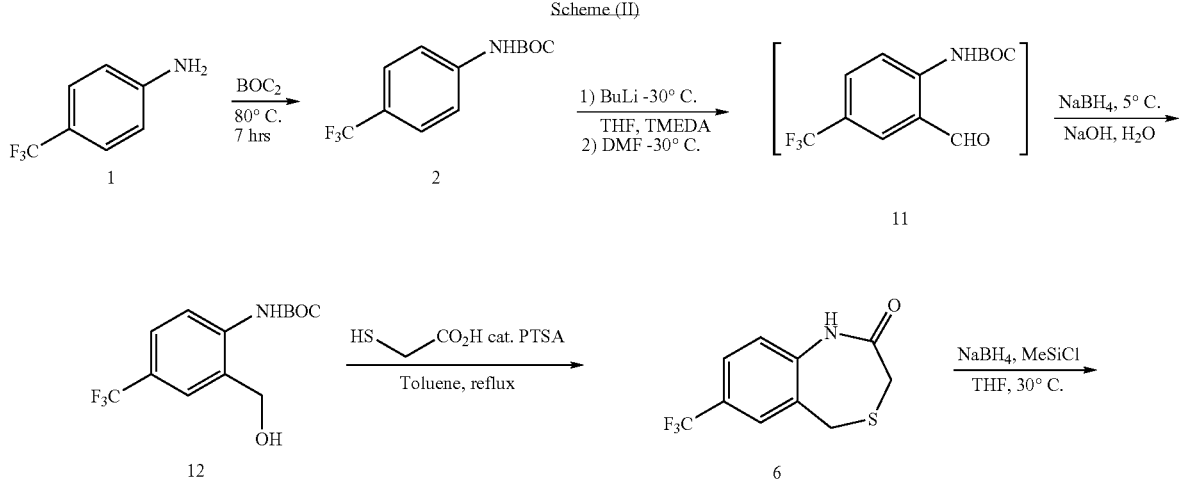

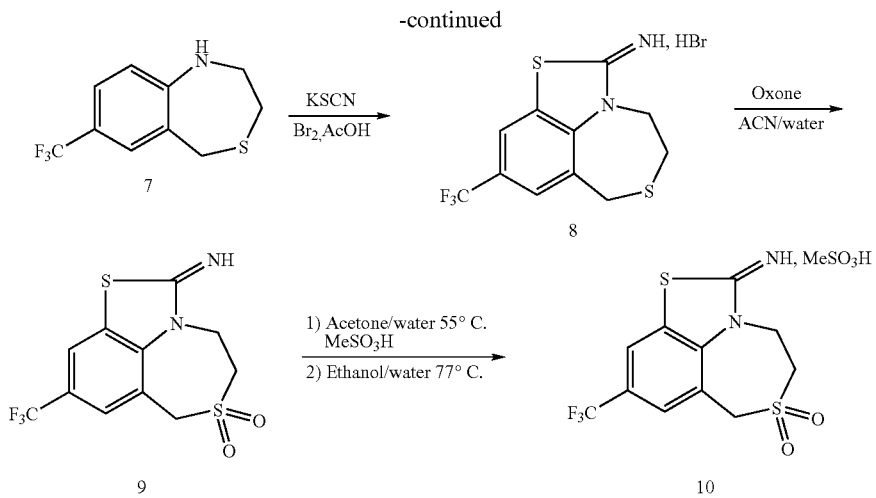

The process for preparing product 10 2-imino-9-trifluoromethyl-4,5-dihydro-2H,7H-thiazolo[3,4,5-de] [4,1]benzothiazepine 6,6-dioxide methanesulfonate is characterized in that a) 4-trifluoromethylaniline 1 is protected in the presence of di-tert-butyl dicarbonate in monochlorobenzene under reflux and then, b) the tert-butyl 4-trifluoromethylphenylcarbamate 2 isolated in the preceding step is converted to 2-hydroxymethyl-4-trifluoromethylphenylcarbamate 12 without isolating the intermediate 2-formyl-4-trifluoromethylphenylcarbamate 11, and then c) the 2-hydroxymethyl-4-trifluoromethylphenylcarbamate 12 isolated in the preceding step is directly converted to 7-trifluoromethyl-1,5-dihydro-3H-[4,1]benzothiazepin-2-one 6 in the presence of thioglycolic acid and a catalytic quantity of p-toluenesulfonic acid, and then d) the 7-trifluoromethyl-1,5-dihydro-3H-[4,1]benzothiazepin-2-one 6 isolated in the preceding step is reduced in order to give 7-trifluoromethyl-1,2,3,5-tetrahydro-[4,1]benzothiazepine 7, and then e) 7-trifluoromethyl-1,2,3,5-tetrahydro-[4,1]benzothiazepine isolated in the preceding step is converted to 8 2-imino-9-trifluoromethyl-4,5-dihydro-2H,7H-thiazolo[3,4,5-de] [4,1]benzothiazepine hydrobromide in the presence of bromine, potassium thiocyanate in acetic acid, and then f) the 2-imino-9-trifluoromethyl-4,5-dihydro-2H,7H-thiazolo[3,4,5-de] [4,1]benzothiazepine hydrobromide is oxidized to 2-imino-9-trifluoromethyl-4,5-dihydro-2H,7H-thiazolo[3,4,5-de] [4,1]benzothiazepine 6,6-dioxide 9 and is then converted in the presence of methanesulfonic acid to 2-imino-9-trifluoromethyl-4,5-dihydro-2H,7H-thiazolo[3,4,5-de] [4,1]benzothiazepine 6,6-dioxide methanesulfonate 10.

The first step consists in protecting the amine functional group of 4-trifluoromethylaniline 1 with di-tert-butyl dicarbonate in monochlorobenzene for 7 hours under reflux between 78 and 82° C. and preferably 80° C. The product is crystallized from methylcyclohexane. The product 2 is obtained with a yield of 88%.

The second step is combined with the third because the intermediate product 11 is not isolated. Product 2 is dissolved in anhydrous tetrahydrofuran (THF) and the solution is cooled to between −32 and −28° and preferably −30°, N,N,N',N'-tetramethylethyldiamine (TMEDA) is added as well as n-butyllithium. After 4 h 30 min at −30°, DMF (dimethylformamide) is added. The treatment is carried out by pouring 6N hydrochloric acid and the whole is heated at 20° C. for 30 min. The aqueous phase is removed and the organic phase is washed with water. The product 11 is thus stored in the cold in THF and is used directly in the next step. To the solution of product 11 in THF at 5° C. is added a mixture of 0.1N sodium hydroxide and $NaBH_4$ at 5° C. After 3 hours at 5° C., a 6N HCl solution is added to the medium and the whole is heated to a temperature of between 18 and 22° C. and preferably 20° C. After decantation and washing with water, the solvent is evaporated and the product is precipitated in the presence of methylcyclohexane. Product 12 is obtained with a yield of 69% in 2 steps.

The fourth step starting with the intermediate 12 consists in forming the second sulfur-containing ring and obtaining product 6. The intermediate 12 in solution in toluene with thioglycolic acid is added to a solution of toluene and p-toluenesulfonic acid under reflux. The whole is kept under reflux. The water is removed using a Dean-Stark during the reaction. At the end of the reaction, the mixture is cooled to a temperature of between 9 and 11° C. and preferably 10° C. and water is added as well as aqueous ammonia. The reaction mixture is treated and the precipitate is washed with water and then dried in order to obtain product 6 with a yield of 84%.

The fifth step starting with the intermediate 6 consists in reducing the amide functional group to an amine. Product 6 is dissolved in THF and $NaBH_4$ is added. The whole is heated to a temperature of between 28° C. and 32° C. and preferably 30° C. and chlorotrimethylsilane is added. After 2 h at 30° C., the medium is cooled to 15° C. A water/THF mixture is added and then sodium hydroxide at 30% to pH 12 over 30 minutes. After decantation, the organic phase is washed with water and an NaCl solution. Product 7 is precipitated in the presence of methanol, is isolated and dried. Product 7 is obtained with a yield of 92%.

The sixth step starting with intermediate 7 consists in forming the third ring and obtaining product 8. The intermediate 7 is solubilized in acetic acid in the presence of potassium thiocyanate. The whole is heated to a temperature of between 29 and 31° C. and preferably 30° C. and a solution of bromine in acetic acid is poured in over 2 hours.

After 2 hours at 30° C., the medium is hydrolyzed by addition of water, and then cooled to a temperature of between 19 and 21° C. and preferably 20° C. The product is filtered, washed with acetic acid and then drained. The cake is then suspended in a water-methanol mixture, and then heated under reflux for 2 hours. After treating with L3S black, the filtrates are concentrated under vacuum in order to remove the methanol. The medium is then cooled to between 4 and 6° C. and preferably 5° C. and is stirred for 30 minutes before being filtered, washed and dried in an oven. Product 8 is obtained with a yield of 57.1%.

The seventh step consists in oxidizing the sulfur, a key intermediate 8, to a sulfone. Product 8 is suspended in a mixture of water and acetonitrile (proportion 12/88). Next, oxone is added in small fractions over 30 min, while the temperature is maintained below a temperature of between 23 and 27° C. and preferably 25° C. The oxidation of the sulfur to a sulfoxide intermediate is complete 10 min after the end of the addition and, after 3 hours of stirring, the sulfoxide intermediate is oxidized to the expected sulfone. The excess oxone is destroyed by adding a 5% aqueous sodium sulfite solution and then the acidic medium is neutralized to pH 9 by adding N sodium hydroxide. The slurry is concentrated at a temperature of between 58 and 62° C. and preferably 60° C. under vacuum to drive the acetonitrile, the aqueous suspension obtained is filtered at a temperature of between 43 and 47° C. and preferably 45° C., the cake is washed with water and then dried in order to obtain the sulfone 9 with a yield of 92%.

The eighth step consists in salifying product 9 and then in recrystallizing the salt obtained. The sulfone 9 is suspended in a mixture of water and acetone, the suspension is heated to 55° C., methanesulfonic acid is then poured in over 10 min, the medium passes into solution, 3S black is added and the suspension obtained is filtered on clarcel. The filtrate is diluted by adding acetone and the medium crystallizes, the temperature is allowed to return to 25° C. then the medium is cooled to 10° C., the slurry is filtered, the cake is washed with acetone and dried under vacuum. The crude product 10 is obtained in the form of a solvate containing 0.2 mol/mol of acetone with a 75% yield.

The suspension of the crude salt 10 in ethanol is heated to 77° C. and then water is rapidly added, the medium passes into solution and then recrystallizes. After maintaining for 15 min at 75° C., the temperature is allowed to return to 25° C. and then the medium is cooled to 10° C., product 10 is isolated and dried. Product 10 is obtained with a recrystallization yield of 75% or an overall yield of step 8 of 56%.

(R,S)-2-Imino-9-trifluoromethyl-4,5-dihydro-2H,7H-thiazolo[3,4,5-de] [4,1]benzothiazepine 6-oxide and its enantiomers may be obtained according to the two procedures described in scheme (III) from the intermediate 8.

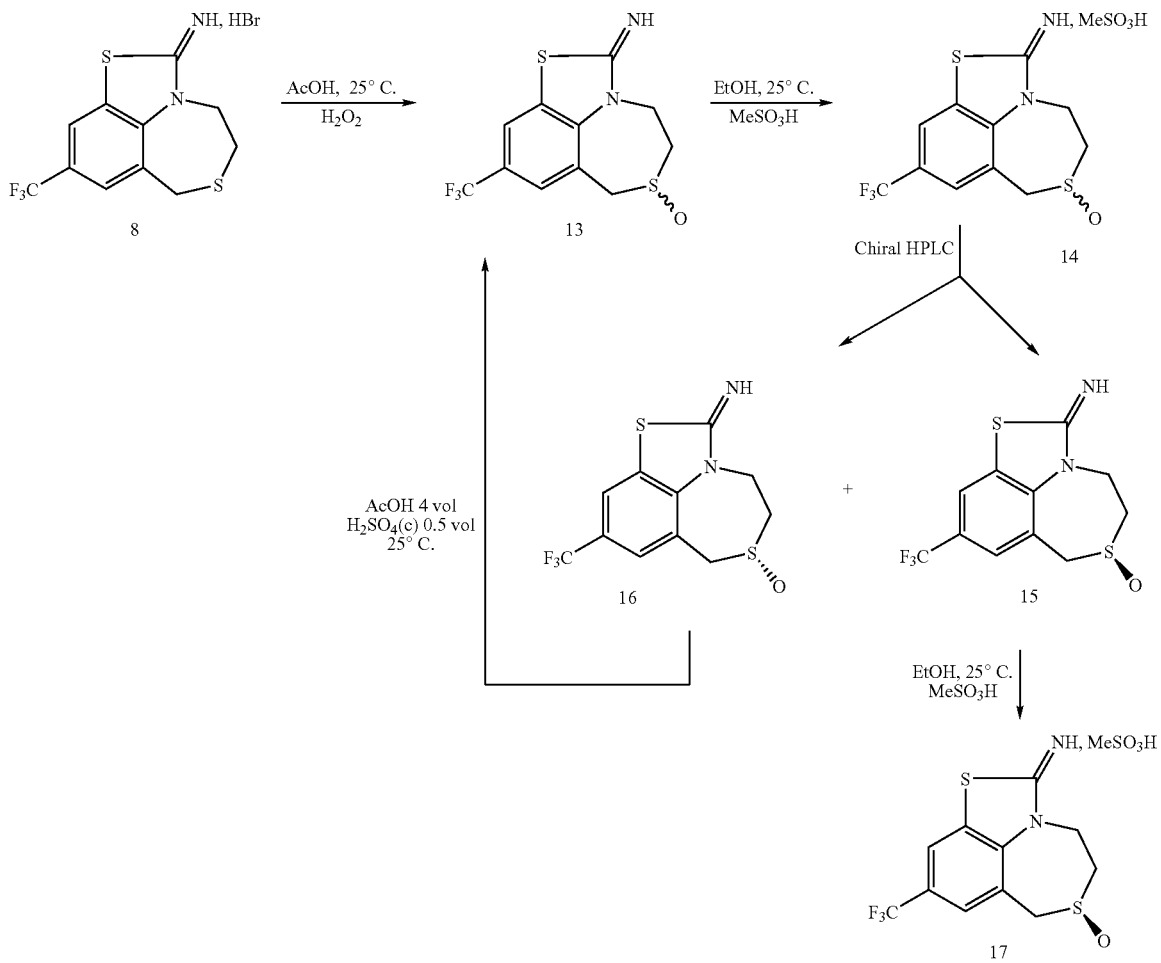

The process for preparing (S)-2-imino-9-trifluoromethyl-4,5-dihydro-2H,7H-thiazolo[3,4,5-de] [4,1]benzothiazepine 6-oxide 16 characterized in that
i) 2-imino-9-trifluoromethyl-4,5-dihydro-2H,7H-thiazolo[3,4,5-de] [4,1]benzothiazepine hydrobromide 8 is mono-oxidized in the form of a racemic to (R,S)-2-imino-9-trifluoromethyl-4,5-dihydro-2H,7H-thiazolo[3,4,5-de] [4,1]benzothiazepine 6-oxide 13, and then
ii) the (R,S)-2-imino-9-trifluoromethyl-4,5-dihydro-2H,7H-thiazolo[3,4,5-de] [4,1]benzothiazepine 6-oxide is converted to a salt of (R,S)-2-imino-9-trifluoromethyl-4,5-dihydro-2H,7H-thiazolo[3,4,5-de] [4,1]benzothiazepine 6-oxide methanesulfonate 14, and then
iii) the (R,S)-2-imino-9-trifluoromethyl-4,5-dihydro-2H,7H-thiazolo[3,4,5-de] [4,1]benzothiazepine 6-oxide methanesulfonate is separated by chiral chromatography to (S)-2-imino-9-trifluoromethyl-4,5-dihydro-2H,7H-thiazolo[3,4,5-de] [4,1]benzothiazepine 6-oxide 15 and (R)-2-imino-9-trifluoromethyl-4,5-dihydro-2H,7H-thiazolo[3,4,5-de] [4,1]benzothiazepine 6-oxide 16, and then
iv) the (S)-2-imino-9-trifluoromethyl-4,5-dihydro-2H,7H-thiazolo[3,4,5-de] [4,1]benzothiazepine 6-oxide is converted to (S)-2-imino-9-trifluoromethyl-4,5-dihydro-2H,7H-thiazolo[3,4,5-de] [4,1]benzothiazepine 6-oxide methanesulfonate 17,
v) the (R)-2-imino-9-trifluoromethyl-4,5-dihydro-2H,7H-thiazolo[3,4,5-de] [4,1]benzothiazepine 6-oxide 16 derived from step iii) is recycled to a racemic (R,S)-2-imino-9-trifluoromethyl-4,5-dihydro-2H,7H-thiazolo[3,4,5-de] [4,1]benzothiazepine 6-oxide which is again separated to (S)-2-imino-9-trifluoromethyl-4,5-dihydro-2H,7H-thiazolo[3,4,5-de] [4,1]benzothiazepine 6-oxide and (R)-2-imino-9-trifluoromethyl-4,5-dihydro-2H,7H-thiazolo[3,4,5-de] [4,1]benzothiazepine 6-oxide.

The synthesis of (R,S)-2-imino-9-trifluoromethyl-4,5-dihydro-2H,7H-thiazolo[3,4,5-de] [4,1]benzothiazepine 6-oxide 13 is carried out starting with 2-imino-9-trifluoromethyl-4,5-dihydro-2H,7H-thiazolo[3,4,5-de]-[4,1]benzothiazepine hydrobromide 8.

The oxidation step for passing from product 8 to product 13 consists in chemically oxidizing the sulfide functional group to a racemic sulfoxide. The oxidation is carried out with hydrogen peroxide in acetic acid at 30° C. A reducing treatment with sodium sulfite is followed by a pouring in of aqueous ammonia in order to bring the pH to 8.5. The product is then filtered, washed several times with water, ethanol and then dried in an oven at 40° C. under an ejecting vacuum. Racemic (R,S)-2-imino-9-trifluoromethyl-4,5-dihydro-2H,7H-thiazolo[3,4,5-de] [4,1]benzothiazepine 6-oxide (1) is obtained with a yield of 94.4%.

The next step consists in converting the (R,S)-2-imino-9-trifluoromethyl-4,5-dihydro-2H,7H-thiazolo[3,4,5-de] [4,1]benzothiazepine 6-oxide to a methanesulfonate salt 14 (R,S)-2-imino-9-trifluoromethyl-4,5-dihydro-2H,7H-thiazolo[3,4,5-de] [4,1]benzothiazepine 6-oxide. To a solution of (R,S)-2-imino-9-trifluoromethyl-4,5-dihydro-2H,7H-thiazolo[3,4,5-de] [4,1]benzothiazepine 6-oxide 13 in ethanol is added at 25° C. methanesulfonic acid. After keeping at this temperature for one hour, the product is filtered, washed with absolute ethanol and then dried in a vacuum oven at 40° C. The (R,S)-2-imino-9-trifluoromethyl-4,5-dihydro-2H,7H-thiazolo[3,4,5-de] [4,1]benzothiazepine 6-oxide methanesulfonate 14 is obtained with a yield of 97.7%.

The next step consists in separating the two enantiomers of (R,S)-2-imino-9-trifluoromethyl-4,5-dihydro-2H,7H-thiazolo[3,4,5-de] [4,1]benzothiazepine 6-oxide methanesulfonate 14 to 15: (S)-2-imino-9-trifluoromethyl-4,5-dihydro-2H,7H-thiazolo[3,4,5-de] [4,1]benzothiazepine 6-oxide and 16: (R)-2-imino-9-trifluoromethyl-4,5-dihydro-2H,7H-thiazolo[3,4,5-de] [4,1]benzothiazepine 6-oxide by chromatography on a Whelk® OI,SS type chiral stationary phase. The eluant for chromatography is prepared by mixing at 25° C. in well-defined proportions water, ethanol and triethylamine. The flushing eluant is prepared by mixing at 25° C. in well-defined proportions water, ethanol, dimethylformamide and triethylamine. The product (R,S)-2-imino-9-trifluoromethyl-4,5-dihydro-2H,7H-thiazolo[3,4,5-de] [4,1]benzothiazepine 6-oxide methanesulfonate is solubilized in the eluant and injected into the column. The fractions containing the product are concentrated under vacuum. At the end of the separation, the elution is reversed in order to recover the other enantiomer 16 (R)-2-imino-9-trifluoromethyl-4,5-dihydro-2H,7H-thiazolo[3,4,5-de] [4,1]benzothiazepine 6-oxide. The product 15 (S)-2-imino-9-trifluoromethyl-4,5-dihydro-2H,7H-thiazolo[3,4,5-de] [4,1]benzothiazepine 6-oxide is obtained with a yield of 45%.

The separation may also be carried out starting with the intermediate (R,S)-2-imino-9-trifluoromethyl-4,5-dihydro-2H,7H-thiazolo[3,4,5-de] [4,1]benzothiazepine 6-oxide free base on a Chiralpack® AD phase with an eluant containing trifluoroacetic acid. Under these conditions, the trifluoroacetate salt of (S)-2-imino-9-trifluoromethyl-4,5-dihydro-2H,7H-thiazolo[3,4,5-de]-[4,1]benzothiazepine 6-oxide is isolated. After returning to the free base with aqueous ammonia, the methanesulfonic acid salt is then prepared.

The next step starting with 15 (S)-2-imino-9-trifluoromethyl-4,5-dihydro-2H,7H-thiazolo[3,4,5-de] [4,1]benzothiazepine 6-oxide consists in preparing the methanesulfonate salt. To a solution of (S)-2-imino-9-trifluoromethyl-4,5-dihydro-2H,7H-thiazolo[3,4,5-de] [4,1]benzothiazepine 6-oxide in ethanol is added at 25° C. methanesulfonic acid. After maintaining for one hour at this temperature, the product is filtered, washed with absolute ethanol and then dried in a vacuum oven at 40° C. The (S)-2-imino-9-trifluoromethyl-4,5-dihydro-2H,7H-thiazolo[3,4,5-de] [4,1]benzothiazepine 6-oxide methanesulfonate 17 is obtained with a yield of 80%.

The intermediate 16 (R)-2-imino-9-trifluoromethyl-4,5-dihydro-2H,7H-thiazolo[3,4,5-de] [4,1]benzothiazepine 6-oxide is recycled in 13 (R,S)-2-imino-9-trifluoromethyl-4,5-dihydro-2H,7H-thiazolo[3,4,5-de] [4,1]benzothiazepine 6-oxide by racemization in acidic medium. The product is solubilized in acetic acid in the presence of sulfuric acid at 25° C. After treatment, the product (R,S)-2-imino-9-trifluoromethyl-4,5-dihydro-2H,7H-thiazolo[3,4,5-de] [4,1]benzothiazepine 6-oxide is isolated with a yield of 90%.

The present invention is illustrated in the examples of synthesis which follow:

Synthesis of 2-imino-9-trifluoromethyl-4,5-dihydro-2H,7H-thiazolo[3,4,5-de] [4,1]benzothiazepine 6,6-dioxide Methanesulfonate Step 1:
Into a 5-liter reactor are loaded 1.6 kg of 4-trifluoromethylaniline 1 at 60.6% in monochlorobenzene and 1.625 kg of di-tert-butyl dicarbonate. The reaction medium is heated to 80+/−2° C. in 1 h 30 min and then kept at this temperature for 6 hours. 2.909 liters of methylcyclohexane are added over 30 minutes and then the medium is cooled to 60° C. over 30 minutes. At this temperature, 1 g of initiator 2 is added and then the medium is cooled to 20+/−5° C. over 2 hours. After cooling to −5+/−1° C. at the rate of 10° C./hour, the medium is kept for 1 hour and then filtered. The cake is washed with 970 ml of methylcyclohexane and then dried in a vacuum oven (5 mbar) at 30–35° C. to constant weight.

1.385 kg of intermediate 2 in the form of white crystals are thus obtained with a yield of 88%.

Step 2:

Into a 1.5-liter reactor are successively loaded at room temperature 400 ml of tetrahydrofuran and 50 g of intermediate 2. The reaction medium is cooled to −30+/−2° C. When the temperature reaches −20° C., 56.16 g of N,N,N,N-tetramethylethylenediamine are loaded while continuing the cooling. When the temperature reaches −30° C., 161.81 g of n-butyllithium in solution at 2.5 M/l in n-hexane are poured in. The medium is stirred at −30+/−2° C. for 4 h 30 min and then 31.09 g of dimethylformamide are then added while the temperature is maintained at −30+/−2° C. After reacting for 30 minutes, 295 ml of precooled 6N hydrochloric acid are poured in at −30° C. The medium is then heated to 20° C. over 1 hour and then stirred for 30 minutes at this temperature before being subjected to decantation. After having removed the aqueous phase, the organic phase is washed twice with 125 ml of demineralized water. The organic phase is then stored at 0–5° C.

436.2 g of a tetrahydrofuran solution of intermediate 11 at 11.47% w/w are thus obtained with a yield of 90.4%.

Step 3:

Into a 100 ml Erlenmeyer flask are loaded at room temperature 24.1 ml of 0.1N sodium hydroxide. After cooling to 5+/−2° C., 4.43 g of sodium borohydride are added. This solution is poured over 1 h 30 min at 5+/−2° C. into a 2-liter reactor containing 436.2 g of tetrahydrofuran solution containing 11.47% w/w of intermediate 11. The medium is then kept at this temperature for 3 hours. The pH of the medium is brought to pH=4 by pouring at 5° C. 21.5 ml of 6N hydrochloric acid. After stirring for 15 minutes, the medium is heated to 20+/−2° C., and then the phases are separated by decantation. The organic phase separated by decantation is then washed with 70 ml of water. The organic phase is then concentrated under 80 mbar without exceeding 35° C. 200 ml of methylcyclohexane are then added to the concentrate and the distillation under reduced pressure is continued. The medium is then cooled to −5+/−2° C. and then filtered. The cake is washed with twice 19 ml of methylcyclohexane, and then drained and dried in a vacuum oven at 30° C.

38.5 g of product 12 are thus obtained in the form of white crystals with a yield of 69% (calculated in 2 steps).

Step 4:

Into a 2-liter reactor are successively loaded 400 ml of toluene and 53.31 g of p-toluenesulfonic acid. The medium is heated under reflux and the solution consisting of 600 ml of toluene, 200 g of intermediate 12 and 96.82 g of thioglycolic acid is poured in over 2 hours. The water generated in the reaction is removed by means of a Dean-Stark. The reaction mass is then cooled to 10+/−1° C. and 300 ml of water are added. 73 ml of 20% aqueous ammonia are poured in so as to bring the pH to 8. After cooling to 5° C., the medium is filtered, washed with 320 ml of water and then 320 ml of toluene. The product is dried in a vacuum oven at 40° C.

143.03 g of product 6: 7-trifluoromethyl-1,5-dihydro-3H-[4,1]benzothiazepin-2-one in the form of a pale yellow powder are isolated with a yield of 84.2%.

Step 5:

Into a 2-liter reactor are successively loaded at room temperature 997 ml of tetrahydrofuran, 100 g of intermediate 6 and 32.68 g of sodium borohydride. The mixture is heated to 30+/−2° C. and 93.88 g of chlorotrimethylsilane are poured in over 1 h 30 min. After keeping for 2 hours at this temperature, the medium is cooled to 15° C. 500 ml of a water-tetrahydrofuran (65/35 v/v) mixture is added over about 2 h 30 min without exceeding a maximum temperature of 20° C. The pH is gradually brought over 30 minutes to 12 by pouring in at 20° C. about 60 ml of 30% sodium hydroxide. After keeping for 30 minutes, the medium is separated by decantation. The organic phase is washed twice with 37 ml of a sodium chloride solution and 180 ml of water. The organic phase is concentrated under vacuum without exceeding a temperature of 30° C. At the end of the concentration, 220 ml of methanol are poured in and the medium is again concentrated. 207 ml of water are then poured in over 15 minutes at 20° C. and the medium is then cooled to 0° C. After keeping for 30 minutes, the medium is filtered and the cake is washed with 72 ml of water and then dried in a vacuum oven at 40° C.

87.67 g of product 7: 7-trifluoromethyl-1,2,3,5-tetrahydro-[4,1]benzothiazepine are obtained with a yield of 91.9%.

Step 6:

Into a 2.5-liter reactor are successively loaded 600 ml of acetic acid, 100 g of intermediate 7-trifluoromethyl-1,2,3,5-tetrahydro-[4,1]benzothiazepine and 94.46 g of potassium thiocyanate. The whole is heated to 30+/−1° C. over 2 hours. The solution consisting of 77.28 g of bromine in 184.8 ml of acetic acid is poured in over 2 hours at 30+/−1° C. After keeping for 2 hours at 30° C., 100 ml of demineralized water are added and the medium is cooled to 20+/−1° C. over 30 minutes. After keeping for 30 minutes at this temperature, the medium is filtered. The cake is washed twice with 2×100 ml of acetic acid. After draining, 253.6 g of crude product 8 is recrystallized from 2.6 liters of a water-methanol (20/8 v/v) mixture. After heating under reflux for 2 hours, 10 g of L3S black and 50 ml of the water-methanol (20/80 v/v) mixture are added and the refluxing is continued for an additional 2 hours. The medium is filtered on a thermostated filter and the cake is washed twice with 2×200 ml of the water-methanol mixture. The filtration juices are then reloaded into a 2.5-liter reactor and concentrated under 15 mbar at a temperature of 45° C. When the methanol content is less than 5% w/w, the medium is cooled to 5+/−1° C. over 1 hour. After keeping at 5° C. for 30 minutes, the medium is filtered and the cake is successively washed at 5° C. with 100 ml of a water-methanol (60/40 v/v) mixture, and then twice with 2×100 ml of acetic acid. The product is then dried in a vacuum oven at 40° C.

88.8 g of product 2-imino-9-trifluoromethyl-4,5-dihydro-2H,7H-thiazolo[3,4,5-de] [4,1]benzothiazepine in the form of a white solid are obtained with a yield of 57.1%.

Step 7:

Into a stirred 6-liter three-necked flask are loaded 9.3 g of 2-imino-9-trifluoromethyl-4,5-dihydro-2H,7H-thiazolo[3,4,5-de] [4,1]benzothiazepine (in hydrobromide form) 8, 164 ml of acetonitrile and 22 ml of water (88/12). To the suspension obtained are added over 30 min in small fractions 24.6 g of oxone while the temperature of the medium is kept <25° C.±2° C. (water bath at 10° C.). During the addition, the suspension thickens and changes from white to yellow.

HPLC performed 10 min after the end of the addition shows that all the 2-imino-9-trifluoromethyl-4,5-dihydro-2H,7H-thiazolo[3,4,5-de] [4,1]benzothiazepine was oxidized to a sulfoxide intermediate. After stirring for 3 hours, the sulfoxide intermediate is oxidized to the expected sulfone 2-imino-9-trifluoromethyl-4,5-dihydro-2H,7H-thiazolo[3,4,5-de] [4,1]benzothiazepine 6,6-dioxide 9.

The excess ozone is destroyed by adding 50 ml of sodium sulfite in a 5% (w/v) aqueous solution until the peroxide test is negative. As soon as the excess of oxidant is destroyed, the color of the slurry passes from yellow to white. The acidic suspension is then neutralized by adding 150 ml of N sodium hydroxide to pH=9.

The suspension is concentrated at 60° C.±2° C. under 40 mmHg in order to expel the acetonitrile. The aqueous suspension obtained is filtered at 45° C.±2° C. on sintered glass, the cake is washed on a filter with 3 times 100 ml of distilled water, thoroughly drained and dried for 72 hours at 35° C.±2° C. under 50 mmHg.

7.4 g of 2-imino-9-trifluoromethyl-4,5-dihydro-2H,7H-thiazolo[3,4,5-de] [4,1]benzothiazepine 6,6-dioxide 9 are obtained with a yield of 92%.

Step 8:

Into a stirred 6-liter three-necked flask are loaded 308.5 g of 2-imino-9-trifluoromethyl-4,5-dihydro-2H,7H-thiazolo[3,4,5-de] [4,1]benzothiazepine 6,6-dioxide 9, 926 ml of acetone and 926 ml of distilled water, the suspension obtained is heated to 55° C.±2° C.; at this temperature 65.9 ml of methanesulfonic acid are poured in over 10 min, the medium passes into solution, 3 g of L3S black are then added and the medium is filtered in the hot state on sintered glass. To the filtrate kept in the hot state are rapidly added 2778 ml of acetone. The medium crystallizes as soon as the addition starts, the temperature of the medium is allowed to return to 25° C.±2° C. and then cooled to 10° C.±2° C. with the aid of an ice bath. The medium is filtered on sintered glass, the drained cake is washed on a filter with 3 times 400 ml of acetone, thoroughly drained and dried for 56 hours at 40° C. under 20 mmHg in a humid water atmosphere.

302 g of crude 2-imino-9-trifluoromethyl-4,5-dihydro-2H,7H-thiazolo[3,4,5-de] [4,1]benzothiazepine 6,6-dioxide methanesulfonate solvated with 0.2 mol/mol of acetone are obtained with a yield of 75%.

Into a stirred 500 ml three-necked flask are loaded 16 g of 2-imino-9-trifluoromethyl-4,5-dihydro-2H,7H-thiazolo[3,4,5-de] [4,1]benzothiazepine 6,6-dioxide methanesulfonate (solvated with 0.2 mol/mol of acetone) and 160 ml of ethanol. The suspension is heated to 77° C.±2° C. (in the region of boiling) and 24 ml of distilled water are added all at once. The medium passes into solution and then recrystallizes immediately, it is left stirring for 15 min at 75° C.±2° C. and then it is allowed to return to room temperature with stirring. The slurry is cooled to 10° C.±2° C., it is filtered on sintered glass and the thoroughly drained cake is dried for 20 hours at 35° C.±2° C. under 20 mmHg.

12 g of 2-imino-9-trifluoromethyl-4,5-dihydro-2H,7H-thiazolo[3,4,5-de] [4,1]benzothiazepine 6,6-dioxide methanesulfonate 10 are obtained with a recrystallization yield of 75%, that is to say an overall yield for step 8 of 56%.

The synthesis of (R,S)-2-imino-9-trifluoromethyl-4,5-dihydro-2H,7H-thiazolo[3,4,5-de] [4,1]benzothiazepine 6-oxide 13 and of its enantiomers were carried out according to the conditions described below.

Into an 8-liter reactor are successively loaded 2.8 liters of acetic acid, 282.27 g of intermediate 8. The medium is heated to 30+/−1° C. and 126.7 g of hydrogen peroxide are added over 1 hour. After keeping for 3 hours at this temperature, the temperature is brought to 20+/−1° C. 14.67 g of sodium sulfite are slowly added and, after keeping for 30 min, 4.55 liters of aqueous ammonia are poured in. After keeping for one hour, the medium is filtered. The cake is successively washed with 282.3 ml of water and then 5.5 ml of absolute ethanol. The product is dried in a vacuum oven at 40° C.

224.37 g of product 13 (R,S)-2-imino-9-trifluoromethyl-4,5-dihydro-2H,7H-thiazolo[3,4,5-de] [4,1]benzothiazepine 6-oxide 13 are obtained in the form of a white powder with a yield of 94.4%.

Into a 2.5 liter reactor are loaded at 25° C. 1012 ml of absolute ethanol and 101.17 g of intermediate 13 (R,S)-2-imino-9-trifluoromethyl-4,5-dihydro-2H,7H-thiazolo-[3,4,5-de] [4,1]benzothiazepine 6-oxide. 34.01 g of methanesulfonic acid are then poured in over 30 min while keeping the temperature at 25+/−1° C. After stirring for one hour, the pH is checked and the medium is filtered. The cake is washed with 50.6 ml of absolute ethanol and then dried in a vacuum oven at 40° C. 129.64 g of product 14 (R,S)-2-imino-9-trifluoromethyl-4,5-dihydro-2H,7H-thiazolo[3,4,5-de] [4,1]benzothiazepine 6-oxide methanesulfonate in the form of a white powder are isolated with a yield of 97.7%.

90 g of intermediate 14 racemic (R,S)-2-imino-9-trifluoromethyl-4,5-dihydro-2H,7H-thiazolo[3,4,5-de] [4,1]benzothiazepine 6-oxide methanesulfonate are dissolved in the eluant consisting of a mixture of 1.2 liters of water and 1.2 liters of ethanol. The solution is filtered before being injected into the column in fractions. The LC80 column is packed at 25° C. with 1.2 kg of Whelk®-01 (S,S) stationary phase in 1.8 liters of absolute ethanol. The elution is carried out with a mixture consisting of 18.7 liters of water, 28.1 liters of absolute ethanol and 94 ml of triethylamine. Alternatively, the elution may be carried out with a mixture consisting of water, absolute ethanol and triethylamine in the proportions 20/80/0.1. The fractions containing the expected product (S)-2-imino-9-trifluoromethyl-4,5-dihydro-2H,7H-thiazolo[3,4,5-de] [4,1]benzothiazepine 6-oxide 15 are assembled and concentrated under vacuum. The precipitate is filtered and washed with water before being dried in a vacuum oven at 30° C. 30.1 g of product (S)-2-imino-9-trifluoromethyl-4,5-dihydro-2H,7H-thiazolo[3,4,5-de]-[4,1]benzothiazepine 6-oxide 15 in the form of white crystals are isolated with a yield of about 45%.

The other enantiomer (R)-2-imino-9-trifluoromethyl-4,5-dihydro-2H,7H-thiazolo[3,4,5-de] [4,1]benzothiazepine 6-oxide may be recovered by reversing the direction of elution and by eluting with a mixture consisting of 0.47 liter of water, 7.9 liters of ethanol, 0.94 liter of dimethylformamide and 18.7 ml of triethylamine.

Into a 2.5-liter reactor are loaded at 25° C. 2494 ml of absolute ethanol and 83.13 g of intermediate (S)-2-imino-9-trifluoromethyl-4,5-dihydro-2H,7H-thiazolo[3,4,5-de] [4,1]benzothiazepine 6-oxide. 28.98 g of methanesulfonic acid are then poured in over 30 min while the temperature is kept at 25+/−1° C. After stirring for 30 min, the solution is filtered on Millipore and then seeded with the pure intermediate (S)-2-imino-9-trifluoromethyl-4,5-dihydro-2H,7H-thiazolo[3,4,5-de] [4,1]benzothiazepine 6-oxide. The stirring is maintained for one hour at 25 μC and then the medium is slowly cooled over 2 hours at 10° C. The medium is then partially concentrated under vacuum until a minimum is reached which can be stirred. After cooling to 5° C. in 1 hour, the precipitate is filtered. The cake is washed with 90 ml of absolute ethanol and then dried in a vacuum oven at 40° C. The product is sieved on a 0.630 mm screen.

87.43 g of product (S)-2-imino-9-trifluoromethyl-4,5-dihydro-2H,7H-thiazolo[3,4,5-de] [4,1]benzothiazepine 6-oxide methanesulfonate in the form of a white powder are isolated with a yield of 80%.

The other enantiomer (R)-2-imino-9-trifluoromethyl-4,5-dihydro-2H,7H-thiazolo[3,4,5-de] [4,1]benzothiazepine 6-oxide 16 is recycled to (R,S)-2-imino-9-trifluoromethyl-4,5-dihydro-2H,7H-thiazolo[3,4,5-de] [4,1]benzothiazepine 6-oxide by solubilizing it in acetic acid in the presence of sulfuric acid at 25° C. After treating in order to neutralize the acidity of the medium, the product (R,S)-2-imino-9-trifluoromethyl-4,5-dihydro-2H,7H-thiazolo[3,4,5-de] [4,1]benzothiazepine 6-oxide is isolated with a yield of 90% which again may be separated into (S)-2-imino-9-trifluoromethyl-4,5-dihydro-2H,7H-thiazolo[3,4,5-de] [4,1]benzothiazepine 6-oxide and (R)-2-imino-9-trifluoromethyl-4,5-dihydro-2H,7H-thiazolo[3,4,5-de] [4,1]benzothiazepine 6-oxide.

Another method for separating the two enantiomers is exemplified below:

The separation may also be carried out with a different chromatographic system starting with the intermediate (R,S)-2-imino-9-trifluoromethyl-4,5-dihydro-2H,7H-thiazolo[3,4,5-de] [4,1]benzothiazepine 6-oxide 13 on a Chiralpack® AD stationary phase with an eluant containing trifluoroacetic acid. The fractions containing the expected product are assembled and concentrated under vacuum. The product is isolated in the form of its trifluoroacetic salt.

The separation may also be carried out with a different chromatographic system starting with the intermediate 13 (R,S)-2-imino-9-trifluoromethyl-4,5-dihydro-2H,7H-thiazolo[3,4,5-de] [4,1]benzothiazepine 6-oxide free base on a Chiralpack® AD stationary phase with an eluant containing trifluoroacetic acid. The fractions containing the expected product (S)-2-imino-9-trifluoromethyl-4,5-dihydro-2H,7H-thiazolo[3,4,5-de] [4,1]benzothiazepine 6-oxide are combined and concentrated under vacuum. The product (S)-2-imino-9-trifluoromethyl-4,5-dihydro-2H,7H-thiazolo[3,4,5-de] [4,1]benzothiazepine 6-oxide is isolated in the form of its trifluoroacetic salt.

The invention claimed is:

1. A process for preparing 2-imino-9-trifluoromethyl-4,5-dihydro-2H,7H-thiazolo[3,4,5-de][4,1]benzothiazepine 6,6-dioxide methanesulfonate wherein
   a) 4-trifluoromethylaniline is protected in the presence of di-tert-butyl dicarbonate in monochlorobenzene under reflux and then,
   b) the tert-butyl 4-trifluoromethylphenylcarbamate isolated in the preceding step is converted to 2-hydroxymethyl-4-trifluoromethylphenylcarbamate without isolating the intermediate 2-formyl-4-trifluoromethylphenylcarbamate, and then
   c) the 2-hydroxymethyl-4-trifluoromethylphenylcarbamate isolated in the preceding step is directly converted to 7-trifluoromethyl-1,5-dihydro-3H-[4,1]benzothiazepin-2-one in the presence of thioglycolic acid and a catalytic quantity of p-toluenesulfonic acid, and then
   d) the 7-trifluoromethyl-1,5-dihydro-3H-[4,1]benzothiazepin-2-one isolated in the preceding step is reduced in order to give 7-trifluoromethyl-1,2,3,5-tetrahydro-[4,1]benzothiazepine, and then
   e) 7-trifluoromethyl-1,2,3,5-tetrahydro-[4,1]benzothiazepine isolated in the preceding step is converted to 2-imino-9-trifluoromethyl-4,5-dihydro-2H,7H-thiazolo[3,4,5-de] [4,1]benzothiazepine hydrobromide in the presence of bromine, potassium thiocyanate in acetic acid, and then
   f) the 2-imino-9-trifluoromethyl-4,5-dihydro-2H,7H-thiazolo[3,4,5-de] [4,1]benzothiazepine hydrobromide is oxidized to 2-imino-9-trifluoromethyl-4,5-dihydro-2H,7H-thiazolo[3,4,5-de] [4,1]benzothiazepine 6,6-dioxide and is then converted in the presence of methanesulfonic acid to 2-imino-9-trifluoromethyl-4,5-dihydro-2H,7H-thiazolo[3,4,5-de] [4,1]benzothiazepine 6,6-dioxide methanesulfonate.

2. The process as claimed in claim 1, wherein tert-butyl 4-trifluoromethylphenylcarbamate is obtained by crystallization from methylcyclohexane.

3. The process as claimed in claim 1, wherein 2-hydroxymethyl-4-trifluoromethylphenylcarbamate is obtained from 2-formyl-4-trifluoromethylphenylcarbamate, obtained by the reaction of n-butyllithium on tert-butyl 4-trifluoromethylphenylcarbamate with dimethylformamide, is not isolated from the reaction medium.

4. A process for the synthesis of 7-trifluoromethyl-1,5-dihydro-3H-[4,1]benzothiazepin-2-one by refluxing from 2-hydroxymethyl-4-trifluoromethylphenylcarbamate in the presence of thioglycolic acid and a catalytic quantity of p-toluenesulfonic acid in toluene under reflux.

5. The process as claimed in claim 1, wherein said 7-trifluoromethyl-1,5-dihydro-3H-[4,1]benzothiazepin-2-one is reduced in the presence of $NaBH_4$ and chlorotrimethylsilane.

6. The process as claimed in claim 1, wherein 2-imino-9-trifluoromethyl-4,5-dihydro-2H,7H-thiazolo[3,4,5-de] [4,1]benzothiazepine hydrobromide is oxidized in the presence of oxone in acetonitrile and water.

7. A process for preparing (S)-2-imino-9-trifluoromethyl-4,5-dihydro-2H,7H-thiazolo[3,4,5-de] [4,1]benzothiazepine 6-oxide wherein
   i) 2-imino-9-trifluoromethyl-4,5-dihydro-2H,7H-thiazolo[3,4,5-de] [4,1]benzothiazepine hydrobromide is mono-oxidized in the form of a racemic mixture to (R,S)-2-imino-9-trifluoromethyl-4,5-dihydro-2H,7H-thiazolo[3,4,5-de] [4,1]benzothiazepine 6-oxide, and then
   ii) the (R,S)-2-imino-9-trifluoromethyl-4,5-dihydro-2H,7H-thiazolo[3,4,5-de] [4,1]benzothiazepine 6-oxide is converted to a salt of (R,S)-2-imino-9-trifluoromethyl-4,5-dihydro-2H,7H-thiazolo[3,4,5-de] [4,1]benzothiazepine 6-oxide methanesulfonate, and then
   iii) the (R,S)-2-imino-9-trifluoromethyl-4,5-dihydro-2H,7H-thiazolo[3,4,5-de] [4,1]benzothiazepine 6-oxide methanesulfonate is separated by chiral chromatography to (S)-2-imino-9-trifluoromethyl-4,5-dihydro-2H,7H-thiazolo[3,4,5-de] [4,1]benzothiazepine 6-oxide and (R)-2-imino-9-trifluoromethyl-4,5-dihydro-2H,7H-thiazolo[3,4,5-de] [4,1]benzothiazepine 6-oxide, and then
   iv) the (S)-2-imino-9-trifluoromethyl-4,5-dihydro-2H,7H-thiazolo[3,4,5-de] [4,1]benzothiazepine 6-oxide is converted to (S)-2-imino-9-trifluoromethyl-4,5-dihydro-2H,7H-thiazolo[3,4,5-de] [4,1]benzothiazepine 6-oxide methanesulfonate,
   v) the (R)-2-imino-9-trifluoromethyl-4,5-dihydro-2H,7H-thiazolo[3,4,5-de] [4,1]benzothiazepine 6-oxide derived from step iii) is recycled to a racemic (R,S)-2-imino-9-trifluoromethyl-4,5-dihydro-2H,7H-thiazolo[3,4,5-de] [4,1]benzothiazepine 6-oxide which is again separated to (S)-2-imino-9-trifluoromethyl-4,5-dihydro-2H,7H-thiazolo[3,4,5-de] [4,1]benzothiazepine 6-oxide and (R)-2-imino-9-trifluoromethyl-4,5-dihydro-2H,7H-thiazolo[3,4,5-de] [4,1]benzothiazepine 6-oxide.

8. The process as claimed in claim 7, wherein the expected product (S)-2-imino-9-trifluoromethyl-4,5-dihydro-2H,7H-thiazolo[3,4,5-de][4,1]benzothiazepine 6-oxide 15 is eluted during chiral chromatography with a mixture consisting of water, absolute ethanol and triethylamine in the proportions 39/59/2.

9. The process as claimed in claim 7, wherein the expected product (S)-2-imino-9-trifluoromethyl-4,5-dihydro-2H,7H-thiazolo[3,4,5-de] [4,1]benzothiazepine 6-oxide 15 is eluted during chiral chromatography in step iii) with a mixture consisting of water, absolute ethanol and triethylamine in the proportions 20/80/0.1.

10. The process as claimed in claim 7, wherein the recycling of step v) is carried out with solubilizing (R)-2-imino-9-trifluoromethyl-4,5-dihydro-2H,7H-thiazolo[3,4,5-de] [4,1]benzothiazepine 6-oxide in acetic acid in the presence of sulfuric acid.

11. The process as claimed in claim 7, wherein oxidation of step i) is carried out with hydrogen peroxide in acetic acid.

12. A process for the synthesis of 2-imino-9-trifluoromethyl-4,5-dihydro-2H,7H-thiazolo[3,4,5-de] [4,1]benzothiazepine hydrobromide, characterized in that
   a) 4-trifluoromethylaniline is protected in the presence of di-tert-butyl dicarbonate in monochlorobenzene under reflux, and then
   b) the tert-butyl 4-trifluoromethylphenylcarbamate isolated in the preceding step is converted to 2-hydroxymethyl-4-trifluoromethylphenylcarbamate without isolating the intermediate 2-formyl-4-trifluoromethylphenylcarbamate, and then
   c) the 2-hydroxymethyl-4-trifluoromethylphenylcarbamate isolated in the preceding step is directly converted to 7-trifluoromethyl-1,5-dihydro-3H-[4,1]benzothiazepin-2-one in the presence of thioglycolic acid and a catalytic quantity of p-toluenesulfonic acid, and then
   d) the 7-trifluoromethyl-1,5-dihydro-3H-[4,1]benzothiazepin-2-one isolated in the preceding step is reduced in order to give 7-trifluoromethyl-1,2,3,5-tetrahydro-[4,1] benzothiazepine, and then
   e) the 7-trifluoromethyl-1,2,3,5-tetrahydro-[4,1]benzothiazepine isolated in the preceding step is converted to 2-imino-9-trifluoromethyl-4,5-dihydro-2H,7H-thiazolo[3,4,5-de] [4,1]benzothiazepine hydrobromide in the presence of bromine, potassium thiocyanate in acetic acid.

13. The intermediate product, 2-imino-9-trifluoromethyl-4,5-dihydro-2H,7H-thiazolo[3,4,5-de] [4,1]benzothiazepine hydrobromide.

14. The intermediate product, the trifluoroacetate salt of (S)-2-imino-9-trifluoromethyl-4,5-dihydro-2H,7H-thiazolo [3,4,5-de] [4,1]benzothiazepine 6-oxide.

* * * * *